(12) United States Patent
Stefanidis

(10) Patent No.: US 11,628,283 B2
(45) Date of Patent: Apr. 18, 2023

(54) MOBILE BALLOON SUPPORT CATHETER

(71) Applicant: SHUTTLE CATHETERS PC, Athens (GR)

(72) Inventor: Giannis Stefanidis, Nea Erythrea Attikis (GR)

(73) Assignee: SHUTTLE CATHETERS PC, Athens (GR)

( * ) Notice: Subject to any disclaimer, the term of this patent is extended or adjusted under 35 U.S.C. 154(b) by 303 days.

(21) Appl. No.: 16/892,025

(22) Filed: Jun. 3, 2020

(65) Prior Publication Data
US 2020/0289798 A1  Sep. 17, 2020

Related U.S. Application Data

(62) Division of application No. 15/736,009, filed as application No. PCT/GR2016/000025 on May 30, 2016, now Pat. No. 10,702,681.

(30) Foreign Application Priority Data

Jun. 17, 2015 (GR) .............................. 20150100278

(51) Int. Cl.
*A61M 25/10* (2013.01)
*A61B 17/3207* (2006.01)
*A61M 25/00* (2006.01)
*A61M 25/09* (2006.01)

(52) U.S. Cl.
CPC ... *A61M 25/104* (2013.01); *A61B 17/320725* (2013.01); *A61M 25/1009* (2013.01); *A61M 25/09* (2013.01); *A61M 2025/0062* (2013.01)

(58) Field of Classification Search
CPC .............. A61M 25/10; A61M 25/1009; A61M 25/104; A61M 2025/0062; A61M 25/09; A61B 17/320725
See application file for complete search history.

(56) References Cited

U.S. PATENT DOCUMENTS 2,936,760 A   5/1960   Gants
4,627,837 A  12/1986   Gonzalo
(Continued)

FOREIGN PATENT DOCUMENTS

EP           1857039 A2    11/2007
WO     WO 2004/026387       4/2004
(Continued)

OTHER PUBLICATIONS

Stefanidis—U.S. Appl. No. 16/325,652, filed Feb. 14, 2019.
(Continued)

*Primary Examiner* — George J Ulsh
(74) *Attorney, Agent, or Firm* — Jason H. Vick; Sheridan Ross, PC

(57) ABSTRACT

The invention refers to endovascular catheters and methods useful to endovascular surgery. In particular, it refers to support catheters with balloons that are used for the placement or the forwarding of the guidewire through demanding tortuosity and important vascular stenoses in cases where the guidewire needs the best possible backup support of the catheter. This is achieved with the development of an endovascular support catheter with a mobile balloon, which has the ability to move along the body of the catheter, at its distal part. The movement of the balloon is achieved with the use of two mobile external rings, one inner wire circuit, and one control handle which is found at the proximal end of the device. The mobile balloon allows the catheter to move inside the vessel even when it is inflated and basically anchored within the vessel.

17 Claims, 10 Drawing Sheets

(56) References Cited

U.S. PATENT DOCUMENTS

| | | | |
|---|---|---|---|
| 4,998,916 | A | 3/1991 | Hammerslag et al. |
| 5,919,163 | A | 7/1999 | Glickman |
| 6,743,208 | B1 | 1/2004 | Coyle |
| 6,730,058 | B2 | 5/2004 | Hayzelden |
| 10,702,681 | B2 | 7/2020 | Stefanidis |
| 2001/0025174 | A1 | 9/2001 | Daniel et al. |
| 2002/0072706 | A1 | 6/2002 | Hiblar et al. |
| 2004/0215140 | A1 | 10/2004 | Forman |
| 2005/0049455 | A1 | 3/2005 | Ootawara et al. |
| 2006/0212022 | A1 | 9/2006 | Gellman |
| 2006/0235368 | A1 | 10/2006 | Oz |
| 2007/0005011 | A1 | 1/2007 | Freyman et al. |
| 2007/0142779 | A1 | 6/2007 | Duane et al. |
| 2014/0276135 | A1 | 9/2014 | Agah et al. |
| 2014/0277071 | A1* | 9/2014 | Wu ................ A61M 25/104 606/192 |
| 2016/0067465 | A1 | 3/2016 | Gerrans et al. |
| 2016/0302762 | A1 | 10/2016 | Stigall et al. |
| 2017/0025933 | A1 | 1/2017 | Fujimaki et al. |
| 2017/0079671 | A1 | 3/2017 | Morero et al. |
| 2017/0259033 | A1 | 9/2017 | Erickson |
| 2018/0071088 | A1 | 3/2018 | Badhwar et al. |
| 2019/0209813 | A1 | 7/2019 | Stefanidis |
| 2019/0345959 | A1 | 11/2019 | Tanaka et al. |
| 2019/0388662 | A1 | 12/2019 | Palushi et al. |

FOREIGN PATENT DOCUMENTS

| | | |
|---|---|---|
| WO | WO 2005/000388 | 1/2005 |
| WO | WO 2016/170446 | 10/2016 |
| WO | WO 2016/203277 | 12/2016 |

OTHER PUBLICATIONS

International Search Report dated Sep. 4, 2017 from related PCT App No. PCT/GR2017/000025.
International Search Report dated Sep. 13, 2016 from related counterpart PCT App No. PCT/GR2016/000025.
Greek Search Report dated Apr. 13, 2016 from counterpart Greek App No. GR20150100278.
Written Opinion for International Application No. PCT/GR2016/000025, dated Sep. 13, 2016.
International Preliminary Report on Patentability for International Application No. PCT/GR2016/000025, dated Dec. 28, 2017.
Intention to Grant for European Application No. 16733176.8, dated Dec. 18, 2018.
Written Opinion for International Application No. PCT/GR2017/000025, dated Sep. 4, 2017.
International Preliminary Report on Patentability for International Application No. PCT/GR2017/000025, dated Mar. 7, 2019.
Office Action for U.S. Appl. No. 15/736,009, dated Nov. 5, 2019.
Notice of Allowance for U.S. Appl. No. 15/736,009, dated Mar. 4, 2020.
Search Report for corresponding Greek Application No. GR20200100742, dated Jun. 9, 2021.
International Search Report for International Application No. PCT/GR2021/000031, dated Nov. 9, 2021.
Written Opinion for International Application No. PCT/GR2021/000031, dated Nov. 9, 2021.
International Search Report for International Application No. PCT/GR2021/000032, dated Nov. 10, 2021.
Written Opinion for International Application No. PCT/GR2021/000032, dated Nov. 10, 2021.
International Search Report for International Application No. PCT/GR2021/000033, dated Nov. 10, 2021.
Written Opinion for International Application No. PCT/GR2021/000033, dated Nov. 10, 2021.
Office Action for U.S. Appl. No. 16/325,652, dated Oct. 6, 2021.
U.S. Appl. No. 15/736,009, filed Dec. 13, 2017 U.S. Pat. No. 10,702,681.
U.S. Appl. No. 16/325,652, filed Feb. 14, 2019.

* cited by examiner

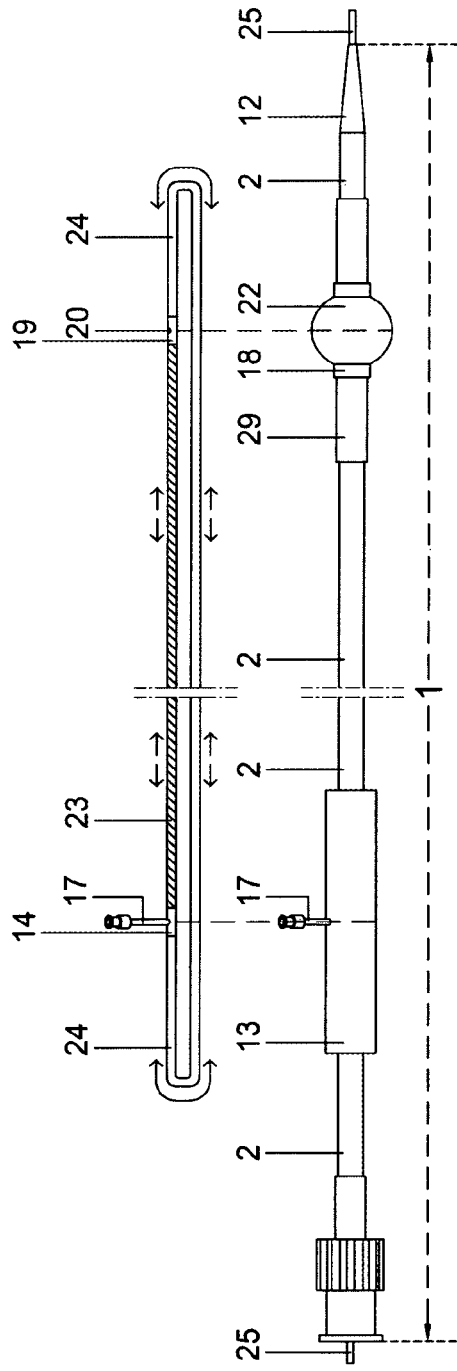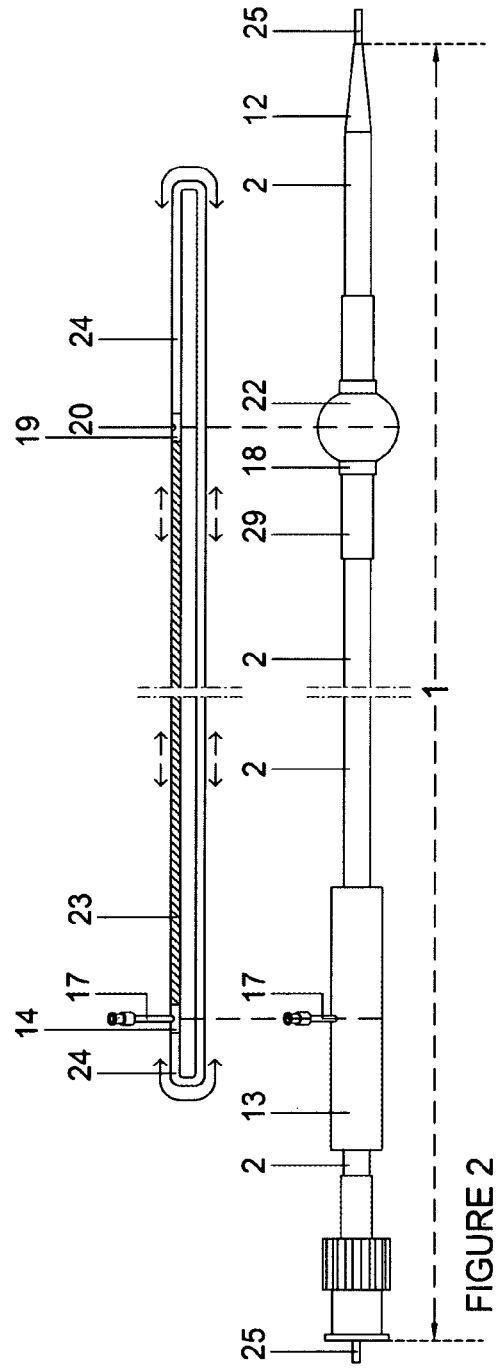

MOBILE BALLOON SUPPORT CATHETER

CROSS-REFERENCE TO RELATED APPLICATIONS

This application is a divisional application of U.S. patent application Ser. No. 15/736,009 filed Dec. 13, 2017, now U.S. Pat. No. 10,702,681, which is a National Phase Application of International Application PCT/GR2016/000025 filed May 30, 2016 which designated the U.S., which claims priority to Greek Patent Application No. 20150100278 filed Jun. 17, 2015. Each of which are incorporated herein by reference in their entirety.

The invention refers to minimally invasive surgical devices and methods, and, specifically, to endovascular balloon catheters that are useful in vascular interventions during endovascular surgery. Specifically, the present invention relates to endovascular balloon catheters and balloon backup support catheters used for the exact positioning of the guidewire within the target vessel or for the crossing of the guidewire through long calcified vascular stenoses, important tortuosity, chronic blockages, vascular bifurcation disorders and generally in cases where the guidewire needs the catheter to provide the maximum possible backup support.

Endovascular surgery is a useful and effective method of dealing with most types of vascular diseases. Generally, the appropriate endovascular device is inserted into the patient's circulatory system, and guided through the vessels, reaches the lesion/stenosis. With the help of endovascular surgery we can reach most parts of the patient's circulatory system, including the heart's coronary vessels, the brain vessels and the peripheral vessels.

Endovascular surgery is a minimally invasive surgical method that was designed to reach, diagnose and treat vessels from within. The recanalization of stenoses or blocked vessels is achieved without the use of general anesthesia, long hospitalization and considerable postoperative pain.

Angioplasty, with or without the deployment of a stent is used for the treatment of chronic blockages, stenoses and other vessel pathologies. During the angioplasty of the coronary, brain or peripheral vessels, an endovascular catheter placed over a guidewire is led to the desired area via the patient's circulatory system. Next, the guidewire, supported by the catheter, is guided through the peripheral opening of the catheter into the target artery (e.g. coronary, brain, renal artery etc.) until it crosses the stenosis or blockage in need of treatment. Following that, a balloon catheter is moved forward over the guidewire that has already crossed the stenosis and is carefully positioned within the blockage. After the catheter has been carefully positioned, the balloon is inflated to a predefined width, pushing the atheromatic material that causes the blockage outwards and opening the artery. The balloon is then deflated, the blood begins to circulate via the opened artery, and the balloon catheter is removed. When needed, after the artery has been opened, a stent may be deployed at the point of the stenosis in order to keep the vessel open for a longer period of time.

Today, balloon catheters are not only used in angioplasty but in a number of other endovascular applications, such as: permanent or temporary blockage of blood flow in a vessel during a neurological brain examination, hemostasis after a vessel rupture (catheters with more than one balloons), embolization of brain aneurisms, blockage of arteriovenous fistula and for the dilation of vessels in vasoconstriction.

Endovascular catheters with or without balloons have been used for years in most endovascular applications and are a basic tool in these treatment approaches. Today, many such different catheters are known and used, and each has certain advantages but also disadvantages. For this reason, there is a great need to develop alternative innovative balloon catheters that will have the advantages of the older ones but will be improved regarding their disadvantages, acquiring greater and new potential.

Endovascular catheters are necessary tools in endovascular surgery; one of their most important uses is the backup support of the guidewire in the surgeon's effort cross through the stenosis—vessel blockage with it. This step proves quite difficult in the anatomically hard to reach regions, in the cases where there are long calcified vascular stenoses, important tortuosity, chronic blockages, vascular bifurcation disorders and generally in the events where the guidewire needs the catheter to provide the maximum possible backup support.

Today, there are endovascular catheters that use modern materials and constructive techniques achieving improved characteristics.

A catheter's most important characteristics are:
1. Pushability: the degree in which the force transmitted from the proximal end of the catheter is translated into the movement of its tip, which depends on the transmission of the force along the body of the catheter.
2. Trackability: the ability of a catheter to follow the guidewire in tortuous vasculature, which depends on the diameter, length and elasticity of the catheter, as well as the resistance caused by friction.
3. Crossability: the ability to navigate the balloon catheter's tip across narrow restrictions in the vasculature.

Today, many different catheters are used in endovascular surgery, each with the abovementioned characteristics in a greater or lesser degree.

The present invention aims to the creation of an endovascular backup support catheter, as described above, that will collectively and maximally present the advantages of an ideal catheter.

A catheter easy to build and use that will provide maximal backup support to the guidewire—when needed—but also the greatest possible pushability, crossability and trackability over a guidewire in tortuous vasculature.

According to the present invention this is achieved with the development of an endovascular mobile balloon catheter, in which the balloon has the ability to move along the body of the catheter at its distal end. The movement of the balloon is accomplished with the help of two external mobile rings, one internal wire circuit, and one control handle which is found at the proximal end of the device. The mobile balloon allows the catheter to move inside the vessel even when it is inflated and basically anchored within the vessel.

A catheter with a balloon that has the ability to move along its body, positioned a few centimeters from the catheter's tip changes the picture, providing the new catheter with great moving and stabilization abilities within the vessel.

By having the balloon inflated and anchored within a vessel, the movement of the balloon in relation to the catheter is translated into the movement of the catheter to the balloon and the vessel—at the same time. Thus, the catheter can move within the vessel accurately and powerfully both forwards and backwards, because of the inflated—anchored balloon. The balloon has a movement range of a few centimeters close to the tip of the catheter. This practically means that the propulsive force that moves the catheter is applied close to its tip, achieving maximal pushability of the tip and therefore of the catheter, since the propulsion force is applied from a distance closer to the tip.

In the present invention, the new catheter can provide backup support to the guidewire in the effort to move it through anatomically difficult areas of the vessels or other lumens of the human body, while—at the same time—it can be accurately repositioned, keeping the balloon inflated and anchored within the vessel.

The catheter acquires greater pushability with the help of the moving balloon, since the propulsive force is applied close to its tip.

As far as crossability is concerned, this new catheter can be moved through significant stenoses by using the propulsive force applied by the moving balloon by pushing the tip of the catheter with greater force.

In the cases of tortuous vasculature, the crossing of the catheter is quite difficult since the friction between the catheter and the vessel, and the catheter and the guidewire multiplies. The trackability of the new mobile balloon support catheter over the guidewire in tortuous vasculature is greater, since once again the propulsive force of the balloon moving close to the tip of the catheter is much greater.

By using the same methodology, the invention can be modified by removing the elastomeric balloon from the low profile mobile ring on which it is loaded so as to load other endovascular tools such as atherectomy blades or use it to unload materials within the vessel.

In the figures that follow, the corresponding reference numbers refer to the same parts, from all different angles. The figures are not drawn necessarily in scale. Instead, the presentation of the principles of the invention has been emphasized. The figures represent typical applications of the invention and should not therefore be considered limiting as to the range of applications. The invention will be described and explained with additional details and accuracy with the use of the attached figures.

FIG. 1 and FIG. 2 are: the detailed illustration of the endovascular mobile balloon support catheter and the illustration of the inner wire circuit that shows the dependent movement of the balloon and the catheter handle button along the catheter to the simultaneous movement of the inner wire circuit, according to the general principles of the invention.

Figure 4:
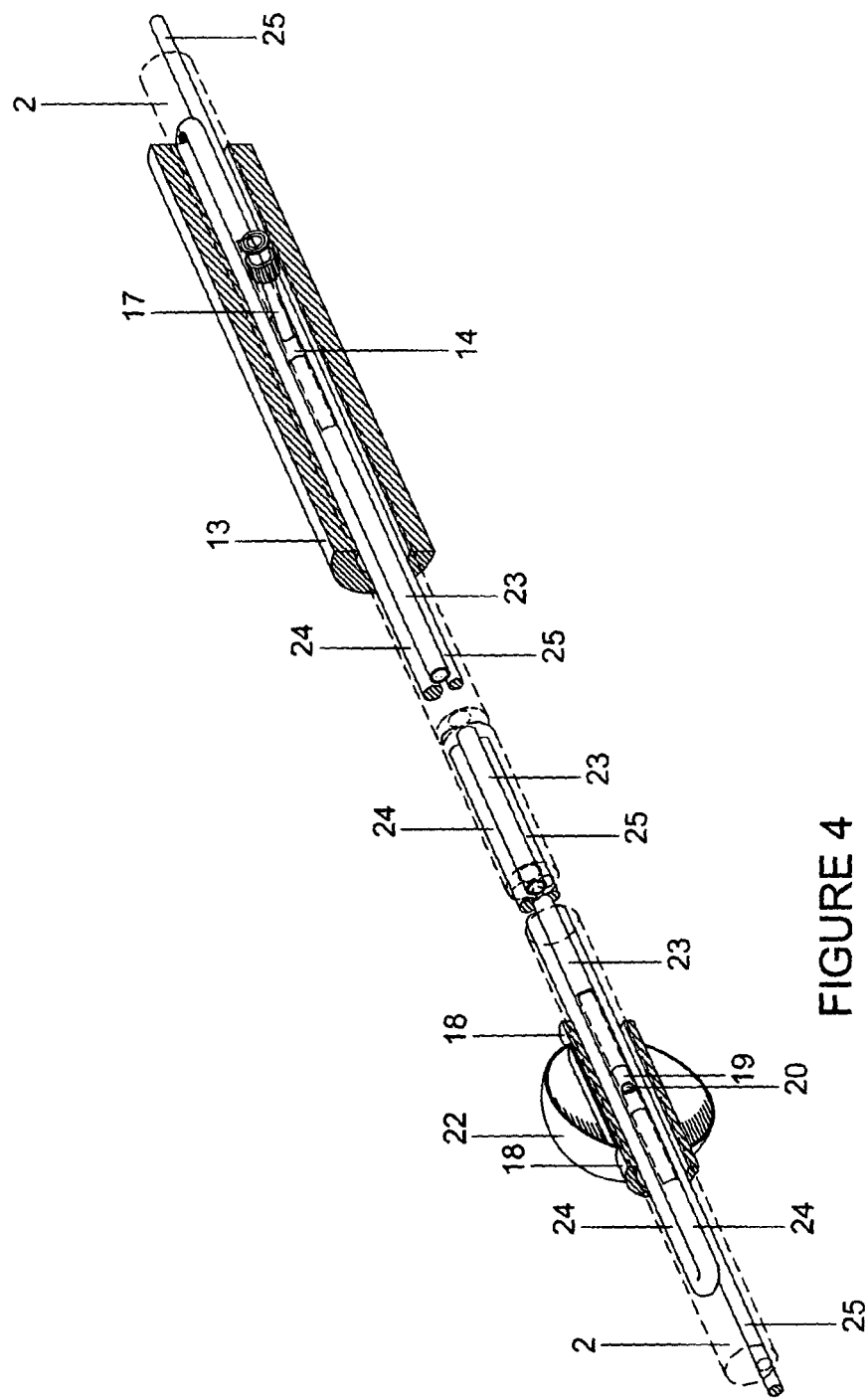

FIG. 4 illustrates—in vertical section—the mobile components of the endovascular mobile balloon support catheter. Specifically, we can see the mobile ring which is used for the movement and the inflation of the mobile balloon along with the system of liquid regulation, the mobile balloon and the mobile ring on which the balloon is loaded, as well as the inner wire circuit that is used to control the movement and the inflation of the balloon.

Figure 5:
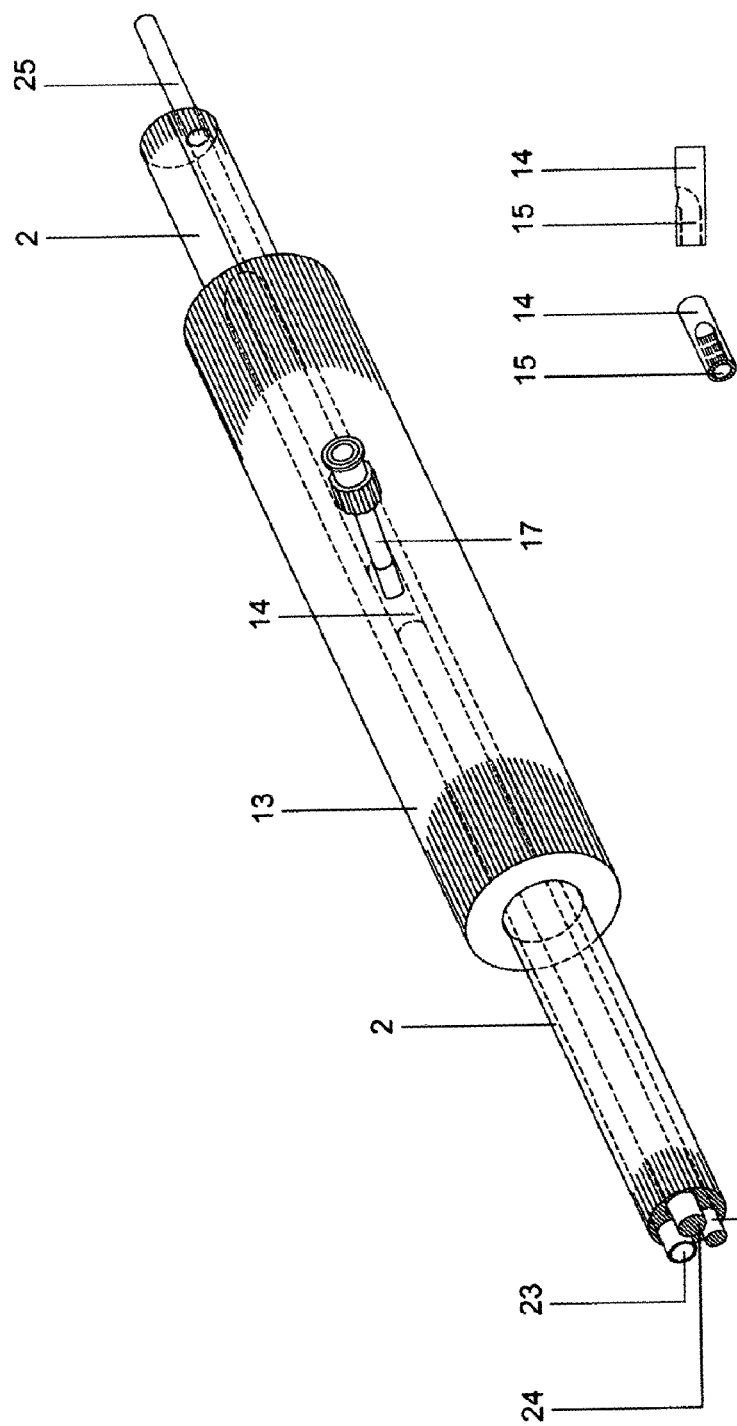

FIG. 5 illustrates the central section of the endovascular mobile balloon support catheter at an angle. Specifically we can see the moving ring which is used for the movement and the inflation of the mobile balloon along with the system of liquid regulation, part of the guidewire and part of the inner wire circuit that is used to control the movement and the inflation of the balloon. There is also a separate figure of the cylindrical part that is attached to the mobile ring, connecting the mobile ring and the system of liquid regulation that inflates the ring to the inner wire system.

Figure 6:
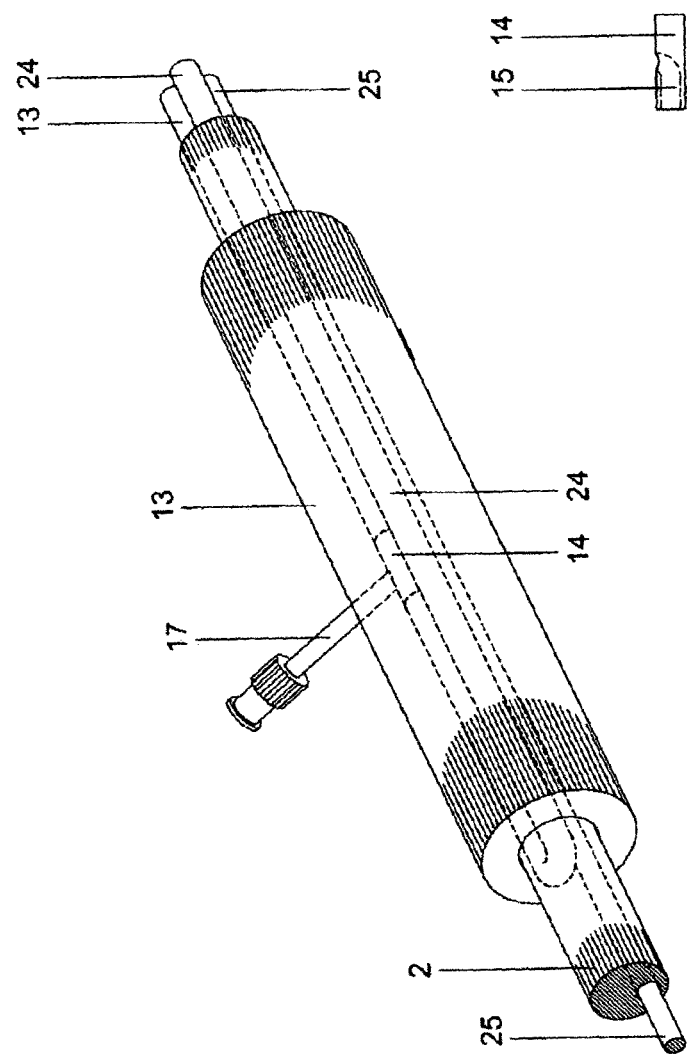

FIG. 6 illustrates the central part of the endovascular mobile balloon support catheter at an angle different to the one of FIG. 5. Specifically, it depicts the mobile ring which is used for the movement and the inflation of the mobile balloon along with the system of liquid regulation, part of the guidewire, and part of the inner wire circuit that is used to control the movement and the inflation of the balloon. The separate figure represents the cylindrical part that is attached to the mobile ring connecting the mobile ring and the system of liquid regulation that inflates the ring to the inner wire system.

Figure 7:
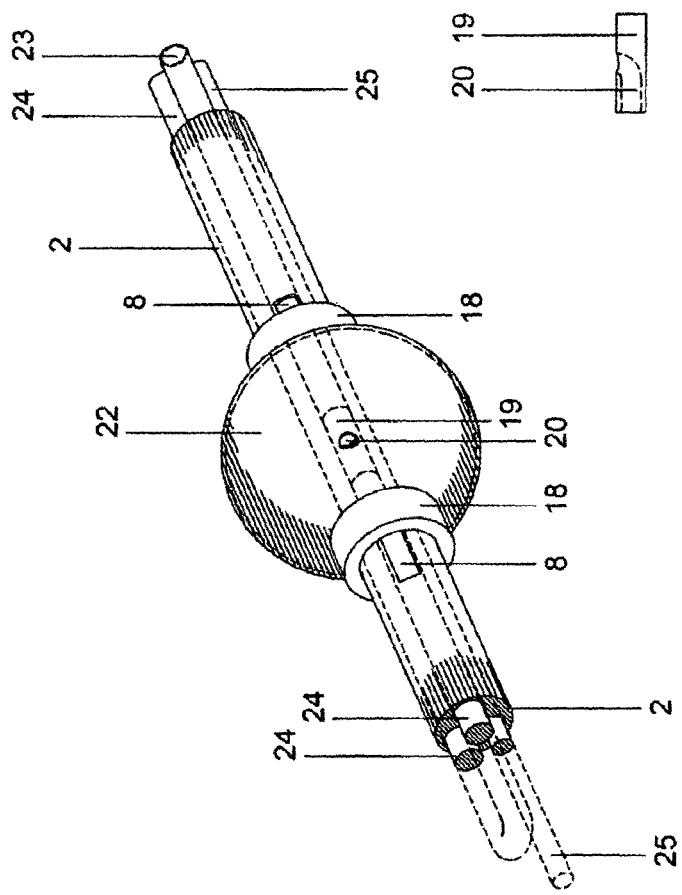

FIG. 7 is an illustration of the peripheral part of the endovascular mobile balloon support catheter at an angle. Specifically, it illustrates the mobile ring and the balloon loaded on it, the peripheral groove of the cylindrical catheter, part of the guidewire and part of the inner wire circuit that is used to control the movement and the inflation of the balloon. On a separate illustration we can see the cylindrical part attached to the mobile balloon ring and connects it to the inner wire circuit.

Figure 8:
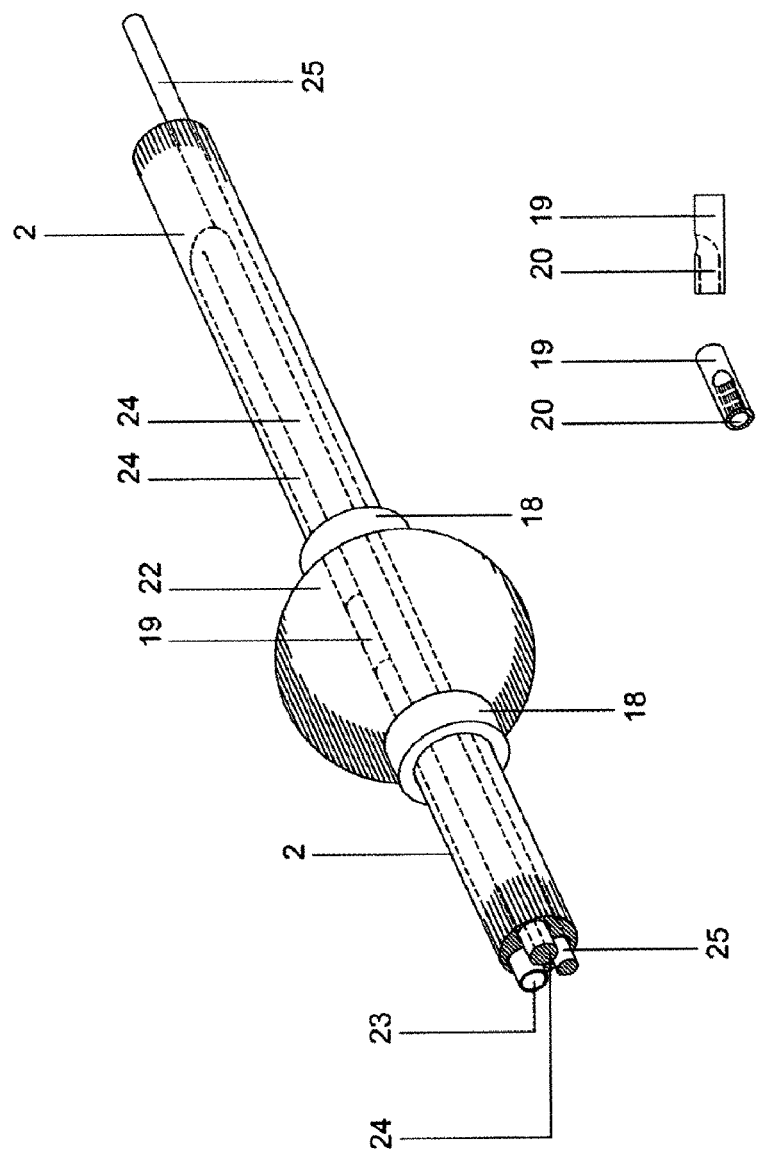

FIG. 8 is an illustration of the peripheral part of the endovascular mobile balloon support catheter at an angle different to the one of FIG. 7. Specifically, it illustrates the mobile ring and the balloon loaded on it, part of the guidewire as well as part of the inner wire circuit that is used to control the movement and the inflation of the balloon. On a separate illustration we can see the cylindrical part attached to the mobile balloon ring and connects it to the inner wire circuit.

Figure 9:
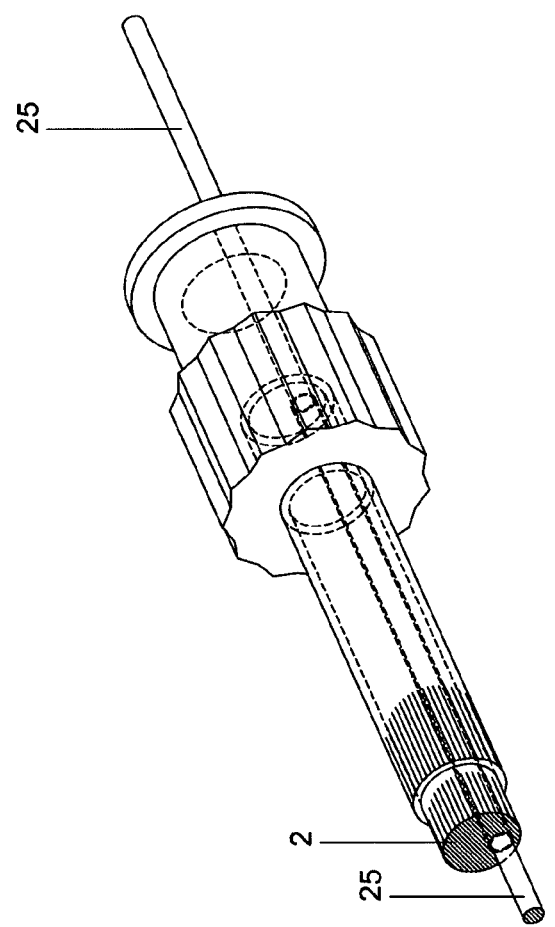

FIG. 9 is an illustration of the point of insertion of the guidewire to the central part of the catheter.

Figure 10:
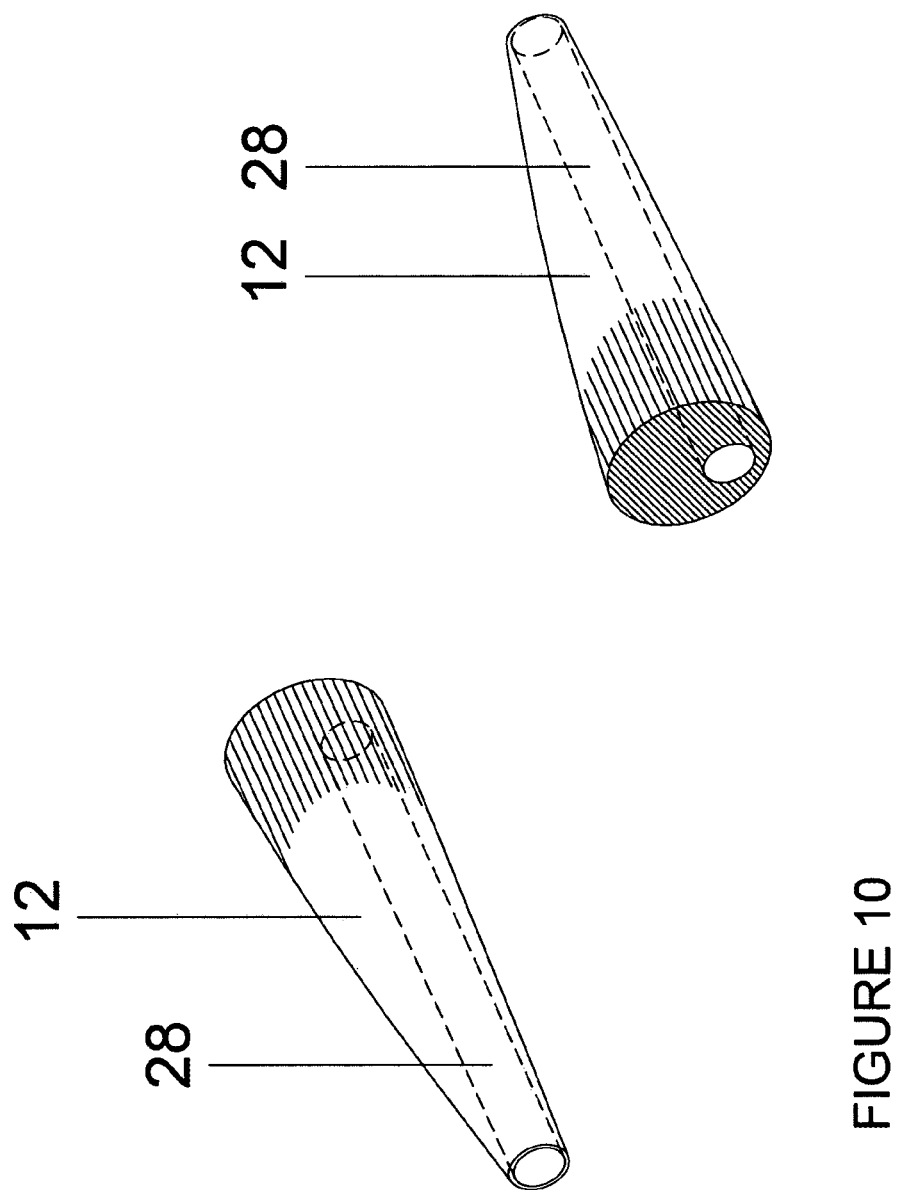

FIG. 10 is an illustration of the specially designed tip at the distal end of the catheter.

Figure 11:
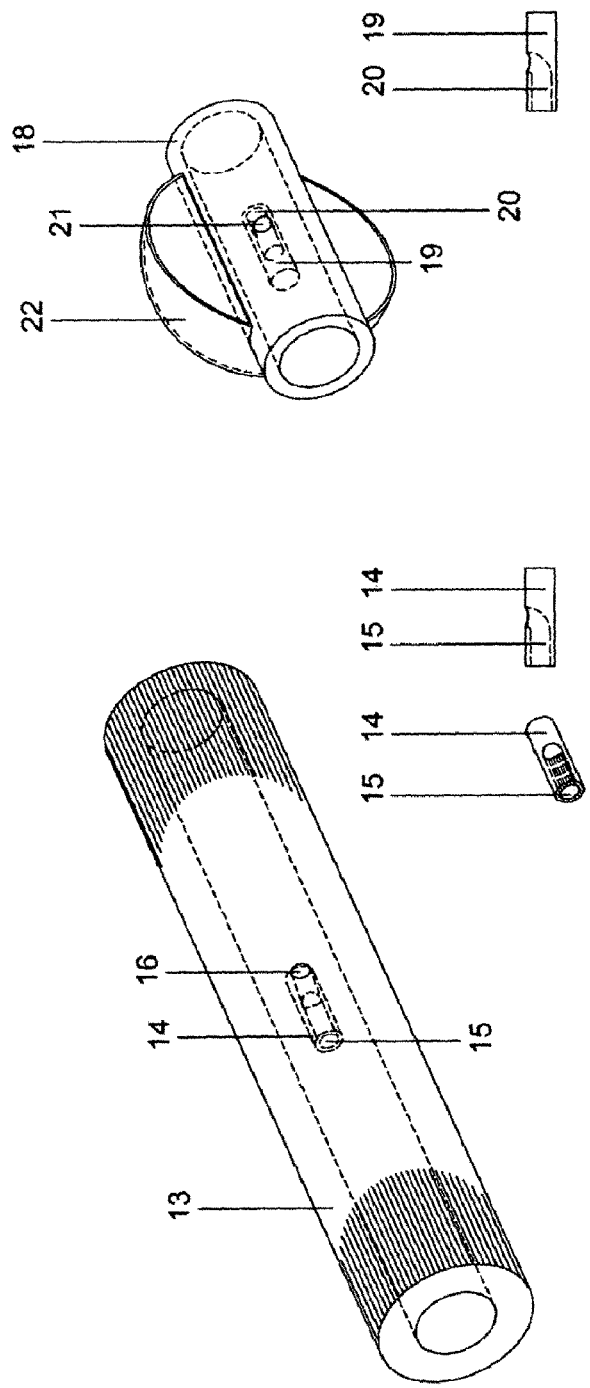

FIG. 11 is an illustration of the mobile ring that controls the balloon and of the mobile ring on which the balloon of the support catheter is loaded. There are further illustrations of the cylindrical parts that are attached inside the mobile rings and connect them to the inner wire circuit.

It is understood that the figures are diagrammatic and schematic representation of exemplary applications of the device and are not limiting as to the range of applications. They are also not drawn in scale.

The present device generally refers to endovascular catheters and methods of using them. More specifically, the present device relates to endovascular balloon catheters and endovascular mobile balloon support catheters that facilitate the exact positioning and crossing of a guidewire through calcified and long lesions, significant tortuous vasculature, chronic blockages, bifurcation lesions and generally help in all cases where the guidewire needs the maximal possible backup support of the catheter. It should be noted that this description is only used as an example and that the present endovascular mobile balloon support catheter can have several applications in the treatment of pathologies in various lumens of the human body, including the ureter and urethra, the cholangi, the esophagus and the tracheobronchial tree.

The endovascular mobile balloon support catheter (1), as illustrated in FIG. 1 and in FIG. 2, has been designed for endoluminal crossing through a vessel and for this reason it can acquire the size that will facilitate this crossing, depending on the vessel in question. For example, for use in a coronary artery, the catheter can have an outside diameter of approximately 1.2 to 1.7 mm and an inside diameter of approximately 0.8 to 1.2 mm, even though these dimensions are purely indicative. For instance, the use of the catheter in non-coronary vessels demands catheter dimensions of a greater scale than the one used for a coronary artery.

Figure 3:
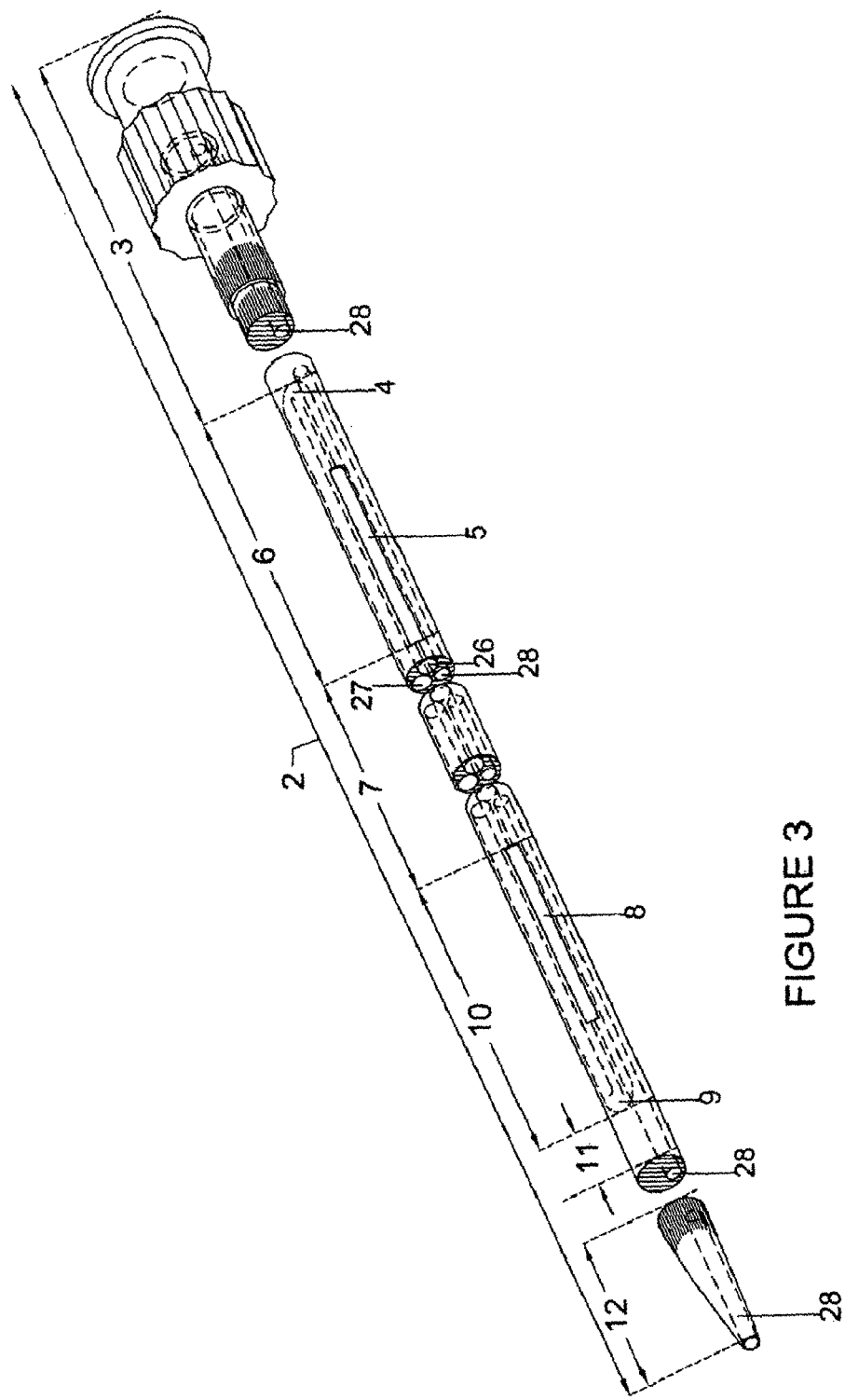
FIG. 3 illustrates the non-mobile components of the endovascular mobile balloon support catheter with the simultaneous representation of their inner lumens. We should note that for the tracking of the device during the endovascular process, some of the catheter's parts are constructed by radiopaque material.

As illustrated in FIG. 1 and FIG. 2, the endovascular mobile balloon support catheter (1) consists of a longitudinal cylindrical catheter (2), partly made of radiopaque material FIG. 3, on which two mobile rings (13) are loaded FIG. 5 and FIG. 6 and (18) FIG. 7 and FIG. 8. The mobile rings (13) and (18) only move along the longitudinal cylindrical catheter (2), without rotating around it. The movement of the mobile rings (13) and (18), is co-dependent and they always move towards the same direction in relation to the longitudinal cylindrical catheter (2), maintaining their in-between distance fixed. This is achieved because of the fact that they form parts of an inner wire circuit, as illustrated in FIG. 1 and FIG. 2. The inner wire system consists of the hollow wire (23) and the synthetic cord (24) that are connected to the mobile rings (13) and (18) via their cylindrical parts (14) and (19) FIG. 11. The mobile ring (13) has an opening (16) FIG. 11, on which the system of liquid regulation that inflates the balloon (17) is affixed. The mobile balloon (22) is loaded to the low profile mobile ring (18).

As described further on, the invention consists of mobile and non mobile components.

Non Mobile Components

As illustrated in FIG. 3, FIG. 9 and in FIG. 10, the longitudinal cylindrical catheter (2) consists of six communicating parts and includes a central cylindrical part (3) FIG. 9, that includes the opening of the lumen (28), through which the guidewire (25) crosses, a cylindrical part (6) with the groove (5) at the proximal part of the catheter, a cylindrical part without a groove (7) at the central part of the catheter, a second cylindrical part (10) with the peripheral groove (8) near the distal end of the longitudinal cylindrical catheter (2), a second cylindrical part without a groove (11) and a specially designed tip (12) FIG. 10 at the very end of the longitudinal cylindrical catheter (2). During the endovascular use, the longitudinal cylindrical catheter (2) can be inserted into the human body by its specially designed tip (12), up to the cylindrical part without groove (7). The cylindrical part (6) and the central cylindrical part (3) are always outside the patient's body, accessible to the surgeon.

The central cylindrical part (3) includes part of the inner lumen (28) that runs along the whole of the longitudinal cylindrical catheter (2), starting at the beginning of the catheter and ending at the last opening of its specially designed tip (12). When the longitudinal cylindrical catheter (2) is being used, the guidewire (25) comes through the inner lumen (28).

The cylindrical part (6), includes parts of the three inner lumens (26), (27), (28), as well as the central groove (5). The central groove (5) is basically an exposed part of the lumen (26) that runs along the cylindrical part (6). The cylindrical part (6) also includes the proximal connection (4) of the lumens (26) and (27).

The cylindrical part (7) includes parts of the inner lumens (26), (27), (28) at its whole length.

The cylindrical part (10) includes parts of the inner lumens (26), (27), (28) as well as the peripheral groove (8). The peripheral groove (8) is basically an exposed part of the lumen (26) that runs along the cylindrical part (10). The cylindrical part with the groove (10) also includes the peripheral connection (9) of the lumens (26) and (27). The cylindrical part (11) includes part of the inner lumen (28) at its whole length. The specially designed tip (12) includes the end part of the inner lumen (28) and is cone-shaped so as to be easily guided within the vessel.

The longitudinal cylindrical catheter (2) includes from one to three inner lumens at its various parts and the two connections (4) and (9) of the two inner lumens. The connections (4) and (9) of the inner lumens (26) and (27) are curved cylindrical parts of inner lumens that connect centrally and peripherally the two parallel lumens (26) and (27). These inner lumens (26), (27) and (28) are parallel to each other and are placed within the catheter as shown in the figures of the device.

Mobile Components

As illustrated in FIG. 1, in FIG. 2, in FIG. 4, in FIG. 5 in FIG. 6, in FIG. 7, in FIG. 8 and in FIG. 11, the endovascular mobile balloon support catheter (1) also includes mobile components. The mobile components are affixed to part (6) and to part (10) of the longitudinal cylindrical catheter (2) FIG. 3. Part (6) includes the mobile ring (13) that facilitates the inflation and the control of the balloon's (22) movement of the endovascular mobile balloon support catheter (1) and part (10) that includes the low profile mobile ring (18) on which the balloon (22) of the endovascular mobile balloon support catheter (1) is loaded.

As illustrated in FIG. 11, inside the mobile ring (13), we find internally affixed the cylindrical component (14) that includes lumen (15). From one side, lumen (15) communicates with the opening (16) of the mobile ring (13) through which enters the liquid that inflates the balloon (22) of the endovascular mobile balloon support catheter (1). The length of the mobile ring (13) is such as to cover the groove (5) whenever it moves.

As illustrated in FIG. 11, inside the low profile mobile ring (18), we find internally affixed the cylindrical part (19) that includes lumen (20). From one side, lumen (20) communicates with the opening (21) of the low profile mobile ring (18) through which enters the liquid that inflates the balloon (22) of the endovascular mobile balloon support catheter (1). The length of the low profile mobile ring (18) can optionally be differentiated with the addition of an extension centrally and peripherally of the mobile ring with a significantly lower profile and greater elasticity (29), so as to cover the groove (8) whenever the balloon moves (FIG. 1, FIG. 2).

As illustrated in FIG. 4, the mobile rings (13) and (18) are connected to each other in a closed circuit with the hollow wire (23) from one side and the synthetic cord (24) at the other side. The hollow wire (23) can only move within the inner lumen (26) when the circuit is in motion, while the synthetic cord (24) can move inside both the two inner lumens (26) and (27), as well as inside the peripheral and central connection (9) and (4) of the inner lumens (26) and (27) FIG. 3. The cylindrical parts (14) and (19) FIG. 11, are fitted inside grooves (5) and (8) FIG. 3, and, therefore, the mobile rings (13) and (18) move within a maximum range delimited by the length of the two exposed parts of the inner lumen (26), i.e. the lengths of grooves (5) and (8).

This new endovascular mobile balloon support catheter (1) can have one external and one internal lining of lubricious material such as Teflon.

The invention claimed is:

1. A surgical device, comprising:
   a cylindrical catheter that extends along a longitudinal axis;
   a first ring which is in contact with and movable along the cylindrical catheter;
   a second, separate, ring which is in contact with and movable along the cylindrical catheter; and
   a surgical tool directly or indirectly attached to the first ring, wherein, the first and second rings are configured so that movement of the second ring in a first direction along the longitudinal axis causes a corresponding movement of the first ring in the same direction along the longitudinal axis, and the cylindrical catheter can be moved through and independent of the first ring.

2. The surgical device of claim 1, wherein the surgical tool is an inflated balloon.

3. The surgical device of claim 2, wherein the inflated balloon becomes anchored.

4. The surgical device of claim 3, wherein the anchored and inflated balloon allows the cylindrical catheter to move accurately and powerfully both forwards and backwards within a vessel or other lumen of the human body.

5. The surgical device of claim 4, wherein the cylindrical catheter is used in angioplasty, for treating vascular disease, or other endovascular applications including permanent or temporary blockage of blood flow in a vessel during a neurological brain examination, hemostasis after a vessel rupture, embolization of brain aneurysms, blockage of arteriovenous fistula and/or for the dilation of vessels in vasoconstriction.

6. The surgical device of claim 1, wherein the surgical tool is a blade.

7. The surgical device of claim 1, wherein the first and second rings can move in either direction along the longitudinal axis and wherein the distance between them remains fixed.

8. The surgical device of claim 1, wherein the surgical tool is used to unload materials within a vessel.

9. A surgical method comprising:
providing a device, comprising:
a cylindrical catheter that extends along a longitudinal axis;
a first ring which is in contact with and movable along the cylindrical catheter;
a second ring which is in contact with and movable along the cylindrical catheter; and
a surgical tool directly or indirectly attached to the first ring,
wherein, the first and second rings are configured so that movement of the second ring in a first direction along the longitudinal axis causes movement of the first ring in the same direction along the longitudinal axis; and
the cylindrical catheter can be moved through and independent of the first ring; and
inserting the portion of the cylindrical catheter in contact with the first ring and the first ring in a human body while maintaining a portion of the cylindrical catheter in contact with the second ring and the second ring outside the human body.

10. The surgical method of claim 9, wherein the surgical tool is an inflated balloon.

11. The surgical method of claim 10, wherein the inflated balloon becomes anchored.

12. The surgical method of claim 11, wherein the anchored and inflated balloon allows the cylindrical catheter to move accurately and powerfully both forwards and backwards within a vessel or other lumen of the human body.

13. The surgical method of claim 12, wherein the cylindrical catheter is used in angioplasty, for treating vascular disease, or other endovascular applications including permanent or temporary blockage of blood flow in a vessel during a neurological brain examination, hemostasis after a vessel rupture, embolization of brain aneurysms, blockage of arteriovenous fistula and for the dilation of vessels in vasoconstriction.

14. The surgical method of claim 9, wherein the surgical tool is a blade.

15. The surgical method of claim 9, wherein the first and second rings can move in either direction along the longitudinal axis and wherein the distance between them remains fixed.

16. The surgical method of claim 9, wherein the surgical tool is used to unload materials within a vessel.

17. A surgical device comprising:
a cylindrical catheter that extends along a longitudinal axis;
a first ring, at a distal end of the cylindrical catheter, which is movable along the cylindrical catheter on the longitudinal axis;
a surgical tool directly or indirectly attached to the first ring; and
a second, independent, ring which is movable along the cylindrical catheter;
wherein, the first and second rings are configured so that movement of the second ring in a first direction along the longitudinal axis causes a corresponding movement of the first ring in the same direction along the longitudinal axis, and the cylindrical catheter can be moved through and independent of the first ring.

* * * * *